US00PP34452P2

(12) United States Plant Patent
DeRoose et al.

(10) Patent No.: US PP34,452 P2
(45) Date of Patent: Jul. 26, 2022

(54) ***CALATHEA* PLANT NAMED 'MYSTY'**

(50) Latin Name: *Calathea roseopicta*
Varietal Denomination: 'Mysty'

(71) Applicants: Reginald Hector K. DeRoose, Evergem (BE); Teunis Valstar, Honserlerdijk (NL)

(72) Inventors: Reginald Hector K. DeRoose, Evergem (BE); Teunis Valstar, Honserlerdijk (NL)

(73) Assignee: DEROOSE PLANTS N.V., Evergem (BE)

( * ) Notice: Subject to any disclaimer, the term of this patent is extended or adjusted under 35 U.S.C. 154(b) by 0 days.

(21) Appl. No.: 17/566,645

(22) Filed: Dec. 30, 2021

Related U.S. Application Data

(60) Provisional application No. 63/133,635, filed on Jan. 4, 2021.

(51) Int. Cl.
*A01H 5/00* (2018.01)

(52) U.S. Cl.
USPC ..... Plt./375

(58) Field of Classification Search
USPC ..... Plt./375
See application file for complete search history.

*Primary Examiner* — Annette H Para
(74) *Attorney, Agent, or Firm* — C. Anne Whealy

(57) ABSTRACT

A new and distinct cultivar of *Calathea* plant named 'Mysty', characterized by its compact and upright to outwardly arching and uniform plant habit; vigorous growth habit; freely clumping growth habit; numerous leaves per plant, densely foliated; developed leaves that are light yellow green, yellow green, medium green and dark green in color arranged in a feather-like pattern; and good interiorscape performance.

2 Drawing Sheets

Figure 1:
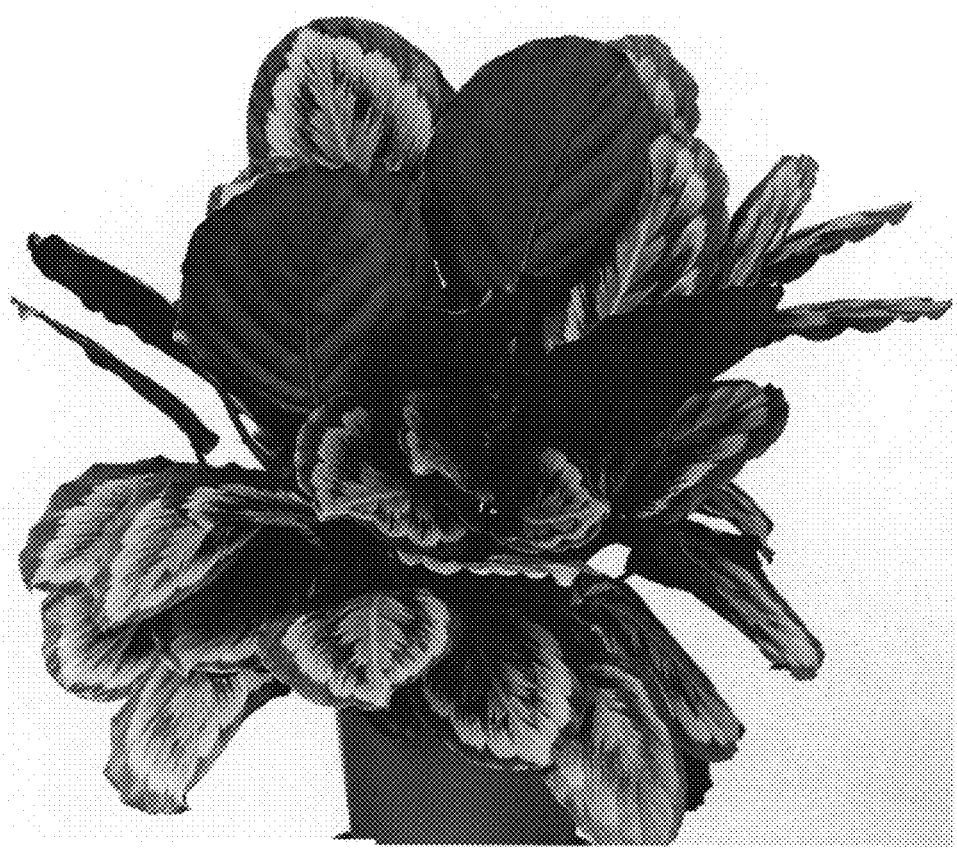

Botanical designation: *Calathea roseopicta.*
Cultivar denomination: 'MYSTY'.

STATEMENT REGARDING PRIOR DISCLOSURES BY INVENTORS/APPLICANTS & ASSIGNEE

An European Community Plant Breeder's Rights application for the instant plant was filed by the Inventors/Applicants and Assignee, DeRoose Plants N.V. of Evergem, Belgium on Nov. 27, 2020, application number 2020/3026. Foreign priority is not claimed to this application.

The Inventors/Applicants and Assignee assert that no publications nor advertisements relating to sales, offers for sale or public distribution occurred more than one year prior to the effective filing date of this application. Any information about the claimed plant would have been obtained from a direct or indirect disclosure from the Inventors/Applicants or Assignee. Inventors/Applicants and Assignee claim a prior art exception under 35 U.S.C. 102(b)(1) for disclosure and/or sales prior to the filing date but less than one year prior to the effective filing date.

BACKGROUND OF THE NEW PLANT

The present invention relates to a new and distinct cultivar of *Calathea* plant, botanically known as *Calathea roseopicta*, commonly referred to as Prayer Plant, commercially produced as a potted plant and hereinafter referred to by the name 'Mysty'.

The new *Calathea* plant is a naturally-occurring whole plant mutation of *Calathea roseopicta* 'Medallion', not patented. The new *Calathea* plant was discovered and selected by the Inventors as a single plant from within a population of plants of 'Medallion' in a controlled greenhouse environment in Evergem, Belgium on Apr. 5, 2016.

Asexual reproduction of the new *Calathea* plant by in vitro meristem culture since May 2, 2017 in a controlled greenhouse environment in Evergem, Belgium, has shown that the unique features of this new *Calathea* plant are stable and reproduced true to type in successive generations of asexual reproduction.

SUMMARY OF THE NEW PLANT

Plants of the new *Calathea* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Mysty'. These characteristics in combination distinguish 'Mysty' as a new and distinct *Calathea* plant:

1. Compact and upright to outwardly arching and uniform plant habit.
2. Vigorous growth habit.
3. Freely clumping growth habit; numerous leaves per plant, densely foliated.
4. Developed leaves that are light yellow green, yellow green, medium green and dark green in color arranged in a feather-like pattern.
5. Good interiorscape performance.

Plants of the new *Calathea* differ primarily from plants of the mutation parent, 'Medallion', in the leaf color and leaf pattern as plants of the new *Calathea* have leaves with yellow green-colored centers surrounded by a narrow dark green-colored band which is surrounded by a broad lighter yellow green-colored band and towards the margins, a broad medium green-colored band whereas leaves of plants of 'Medallion' have yellow green-colored centers surrounded by a broad dark green-colored band which is surrounded by a narrow lighter yellow green-colored band and towards the margins, a broad medium green-colored band.

Plants of the new *Calathea* can also be compared to plants of *Calathea roseopicta* 'Shinestar', not patented. In side-by-side comparisons plants of the new *Calathea* differ primarily from plants of 'Shinestar' in the leaf color and leaf pattern as plants of the new *Calathea* have leaves with yellow green-colored centers surrounded by a narrow dark green-colored band which is surrounded by a broad lighter yellow green-colored band and towards the margins, a broad medium green-colored band whereas leaves of plants of 'Shinestar' have narrow yellow green-colored centers surrounded by a very broad dark green-colored band which is surrounded by a lighter yellow green-colored band and towards the margins, a very narrow green-colored band.

BRIEF DESCRIPTION OF THE PHOTOGRAPHS

The accompanying photographs illustrate the overall appearance of the new *Calathea* plant showing the colors as true as it is reasonably possible to obtain in colored reproductions of this type. Colors in the photographs may differ slightly from the color values cited in the detailed botanical description which accurately describe the colors of the new *Calathea* plant.

The photograph on the first sheet (FIG. 1) is a side perspective view of a typical plant of 'Mysty' grown in a container and is the same photograph as filed in the U.S. Provisional Patent application Ser. No. 63/133,635.

Figure 2:
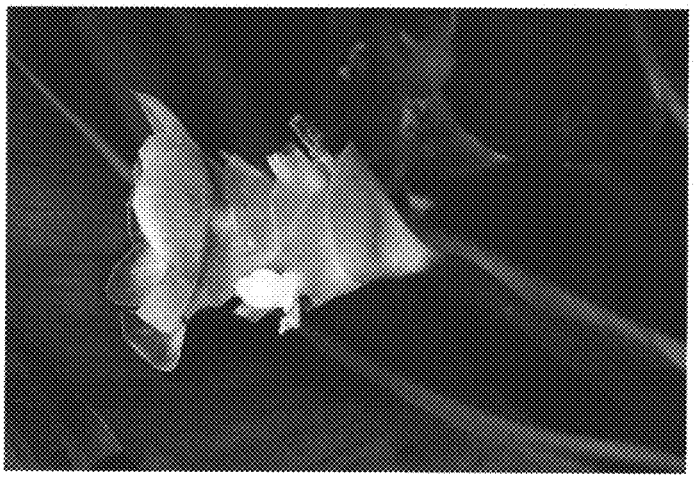

The photograph on the left of the second sheet (FIG. 2) is a close-up view of a typical inflorescence of 'Mysty'.

Figure 3:
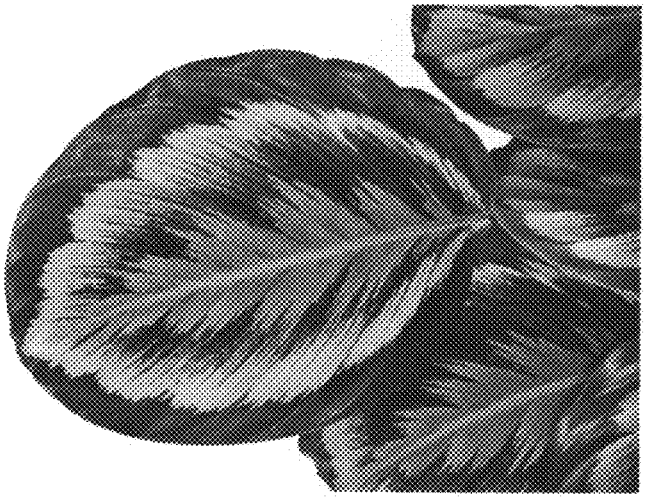

The photograph at the center of second sheet (FIG. 3) is a close-up view of the upper surface of typical leaves of 'Mysty'.

Figure 4:
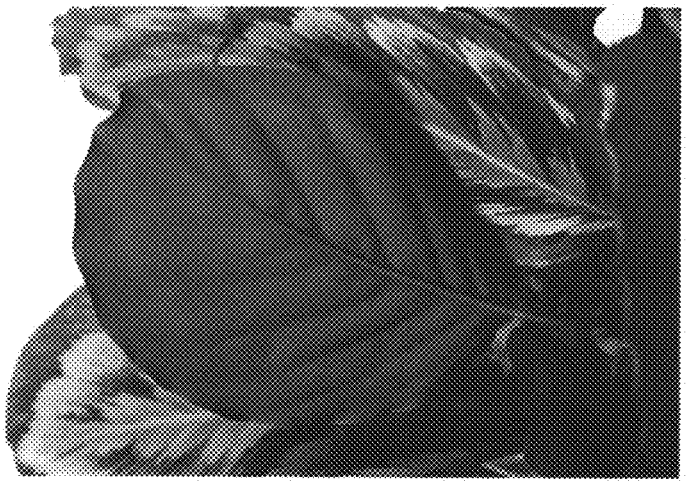

The photograph on the right of second sheet (FIG. 4) is a close-up view of the lower surface of a typical leaf of 'Mysty'.

DETAILED BOTANICAL DESCRIPTION

The aforementioned photographs and following observations and measurements describe plants grown during the late summer and early autumn in 21-cm containers in a glass-covered greenhouse in Evergem, Belgium and under cultural practices typical of commercial *Calathea* production. During the production of the plants, day temperatures ranged from 19° C. to 29° C. and night temperatures ranged from 16° C. to 22° C. Plants were 45 weeks old when the photographs and the detailed description were taken. In the following description, color references are made to The Royal Horticultural Society Colour Chart, 2015 Edition, except where general terms of ordinary dictionary significance are used.

Botanical classification: *Calathea roseopicta* 'Mysty'.

Parentage: Naturally-occurring whole plant mutation of *Calathea roseopicta* 'Medallion', not patented.

Propagation:

*Type.*—By in vitro meristem culture.

*Time to initiate roots.*—About 16 days at temperatures about 23° C.

*Time to produce a rooted young plant.*—About 14 to 18 days at temperatures about 20° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching, medium density.

Plant description:

*Plant and growth habit.*—Compact and upright to outwardly arching and uniform plant habit; overall shape, flattened globular; freely clumping habit with about 14 basal shoots forming per plant; vigorous growth habit and moderate to rapid growth rate.

*Plant height* (*soil level to top of foliar plane*).—About 42.5 cm.

*Plant height* (*soil level to top of floral plane*).—About 31 cm.

*Plant diameter.*—About 79.6 cm.

Leaf description:

*Leaf arrangement.*—Alternate; simple.

*Length, fully expanded.*—About 23.2 cm.

*Width, fully expanded.*—About 17.7 cm.

*Shape.*—Broadly elliptic to broadly obovate.

*Apex.*—Abruptly acute.

*Base.*—Rounded to shallow truncate.

*Margin.*—Entire to crenate; moderately undulate.

*Venation.*—Pinnate.

*Aspect.*—Initially upright, then outwardly arching.

*Texture and luster, upper surface.*—Smooth, glabrous; non-rugose; slightly glossy.

*Texture and luster, lower surface.*—Smooth, glabrous; non-rugose; matte.

*Color.*—Developing leaves, upper surface: Center: Close to 146C to 146D. Band surrounding center: Irregularly blotched with between 143A and 146A. Band surrounding previous band: Close to N148D. Band towards the margin: Close to between 139A and NN137A. Leaf edge: Close to 146A. Developing leaves, lower surface: Center: Close to N77D. Band surrounding center: Irregularly blotched with slightly darker than N77C. Band surrounding previous band: Close to N77B. Band towards the margin: Close to between N186C and N77C. Fully expanded leaves, upper surface: Center: Close to 137C. Band surrounding center: Irregularly blotched with between 139A, N189A and NN137A. Band surrounding previous band: Close to 148D. Band towards the margin: Close to between 139A and N189A. Leaf edge: Slightly darker than 137A. Midvein: Close to 148A to 148B. Lateral venation: Close to 139A. Fully expanded leaves, lower surface: Close to between 187A and N187A and towards the margin, slightly darker than N187A; midvein, close to between 177C and 199B and lateral venation, close to N186B.

*Petioles.*—Length: About 25.8 cm. Width: About 7 mm by 8 mm. Texture and luster, upper and lower surfaces: Smooth, glabrous; glossy. Strength: Moderately strong. Color, upper and lower surfaces: Close to between N186C and 200A and proximally, close to N186C.

*Wings.*—Length: About 8.9 cm. Width: About 7 mm. Texture and luster, upper surface: Smooth, glabrous; moderately glossy. Texture and luster, lower surface:

Smooth, glabrous; glossy. Color, upper surface: Close to 183B to 183C. Color, lower surface: Close to 187C to 187D.

*Geniculum.*—Length: About 5.1 cm. Width: About 6 mm. Texture, upper and lower surfaces: Smooth, glabrous. Color, upper and lower surfaces: Close to 200C.

Inflorescence description:

*Arrangement.*—Upright terminal compound spike inflorescences developing directly from the basal shoots; typically each spike with about 39 flowers and about 468 flowers buds and flowers developing per plant during the flowering season.

*Time to flower.*—In The Netherlands, plants flower from summer into autumn; flowering continuous during this period.

*Flower longevity.*—Flowers last about three days on the plant; flowers persistent; plants maintain good substance for about 120 days.

*Fragrance.*—None detected.

*Flower buds.*—Length: About 3.3 cm. Diameter: About 6 mm. Shape: Narrowly oblong. Texture and luster: Smooth, glabrous; glossy. Color: Immature sepals, close to 146D and 150D.

*Inflorescence length.*—About 6.2 cm.

*Inflorescence diameter.*—About 5.6 cm.

*Flowers.*—Shape and arrangement: Corolla cruciform with four petals; one upper petal, one lower petal and two lateral petals fused towards the base with 30% of the petals free. Diameter: About 1.2 cm by 2.1 cm. Depth: About 3.4 cm. Flower throat diameter: About 2 mm. Flower tube length: About 1.9 cm. Flower tube diameter: About 2 mm.

*Upper petal.*—Length: About 1 cm. Width: About 8 mm. Shape, free part: Broadly obovate. Apex: Emarginate. Margins: Entire; slightly undulate. Texture and luster, upper surface: Smooth, glabrous; slightly velvety; matte. Texture and luster, lower surface: Smooth, glabrous; slightly glossy. Color: When opening and fully opened, upper surface: Close to NN155C slightly tinged with close to N77D; venation, similar to lamina color; color does not change with subsequent development. When opening and fully opened, lower surface: Close to NN155B slightly tinged with close to 76A; venation, similar to lamina color; color does not change with subsequent development.

*Lower petal.*—Length: About 1.1 cm. Width: About 5.5 mm. Shape, free part: Obovate. Apex: Obtuse. Margins: Entire; slightly undulate. Texture and luster, upper surface: Smooth, glabrous; slightly velvety; matte. Texture and luster, lower surface: Smooth, glabrous; slightly glossy. Color: When opening and fully opened, upper surface: Close to N77D and towards the margin, close to N155B; venation, similar to lamina color; color does not change with subsequent development. When opening and fully opened, lower surface: Close to 76A; venation, similar to lamina color; color does not change with subsequent development.

*Lateral petals.*—Length: About 5 mm. Width: About 2 mm. Shape, free part: Narrowly elliptic. Apex: Acute. Margins: Entire; not undulate. Texture and luster, upper surface: Smooth, glabrous; slightly velvety; matte. Texture and luster, lower surface: Smooth, glabrous; slightly glossy. Color: When opening and fully opened, upper surface: Close to N155C; venation, similar to lamina color; color does not change with subsequent development. When opening and fully opened, lower surface: Close to N155B; venation, similar to lamina color; color does not change with subsequent development.

*Flower throat.*—Texture: Smooth, glabrous. Color: Close to NN155B.

*Flower tube.*—Texture: Smooth, glabrous. Color: Close to 157A.

*Sepals.*—Quantity of sepals and arrangement: Three in a single whorl; fused towards the base with 30% of the sepals free. Length: About 9 mm. Diameter: About 3 mm. Shape: Narrowly ovate. Apex: Acute. Base: Broadly cuneate. Margin: Entire. Texture and luster, upper surface: Smooth, glabrous; moderately glossy. Texture and luster, lower surface: Smooth, glabrous; glossy. Color: When opening and fully opened, upper surface: Close to 157D. When opening and fully opened, lower surface: Close to 157D.

*Upper flower bracts.*—Quantity: About seven upper bracts per inflorescence. Length: About 3.1 cm. Width: About 2.3 cm. Shape: Ovate; slightly concave. Apex: Broadly acute. Base: Truncate. Margin: Entire. Texture and luster, upper and lower surfaces: Smooth, glabrous; matte. Color: When opening and fully opened, upper surface: Close to 147D with broad margins, close to 146A. When opening and fully opened, lower surface: Close to 148D with broad margins, close to 147B.

*Lower flower bracts.*—Quantity: About 13 lower bracts per inflorescence. Length: About 2.4 cm. Width: About 3.6 cm. Shape: Reniform to close to flabellate; strongly concave. Apex: Obtuse. Base: Cuneate. Margin: Entire. Texture and luster, upper surface: Smooth, glabrous; moderately glossy. Texture and luster, lower surface: Smooth, glabrous; slightly glossy. Color: When opening and fully opened, upper surface: Close to 144A. When opening and fully opened, lower surface: Close to 146B.

*Peduncles.*—Length: About 20.6 cm. Diameter: About 6 mm. Strength: Strong. Aspect: Mostly erect. Texture and luster: Smooth, glabrous; moderately glossy. Color: Close to between N186C and 200A.

*Stamens.*—Quantity: One per flower; appressed to flower throat. Filament length: About 3 mm. Filament color: Close to NN155C. Anther size: About 0.5 mm by 2.5 mm. Anther shape: Narrowly oblong. Anther color: Close to 158C. Pollen amount: Sparse. Pollen color: Close to 164C.

*Pistils.*—Quantity per flower: One. Pistil length: About 2.5 cm. Style length: About 2.3 cm. Style color: Close to 155C. Stigma diameter: About 1 mm. Stigma shape: Club-shaped. Stigma color: Close to 156D. Ovary color: Close to 155D.

*Seeds and fruits.*—To date, seed and fruit development have not been observed on plants of the new *Calathea.*

Pathogen & pest resistance: To date, plants of the new *Calathea* have not been observed to be resistant to pathogens or pests common to *Calathea* plants.

Temperature tolerance: Plants of the new *Calathea* have been observed to be tolerant to temperatures ranging from about 8° C. to about 40° C. and are suitable for USDA Hardiness Zones 10 to 13.

It is claimed:

1. A new and distinct *Calathea* plant named 'Mysty' as illustrated and described.

* * * * *